United States Patent [19]

Baumhöfer et al.

[11] Patent Number: 5,240,053
[45] Date of Patent: Aug. 31, 1993

[54] TIRE TREAD WITH SPACED CENTRAL TREAD NARROW GROOVES

[75] Inventors: Johannes Baumhöfer; Joachim Bellut; Dionysius Poque; Helmut Rickling, all of Aachen, Fed. Rep. of Germany

[73] Assignee: Uniroyal Englebert Reifen GmbH, Aachen, Fed. Rep. of Germany

[21] Appl. No.: 710,780

[22] Filed: Jun. 5, 1991

[30] Foreign Application Priority Data

Dec. 4, 1990 [DE] Fed. Rep. of Germany ... 9016455[U]

[51] Int. Cl.$^5$ .............................................. B60C 11/11
[52] U.S. Cl. ................................................. 152/209 R
[58] Field of Search ........... 152/209 R, 209 A, 209 D; D12/146–148

[56] References Cited

U.S. PATENT DOCUMENTS

| D. 261,497 | 10/1981 | Baus et al. | D12/145 |
| D. 265,302 | 7/1982 | Kojima et al. | D12/147 |
| D. 279,366 | 6/1985 | Takehara | D12/145 |
| D. 286,274 | 10/1986 | Davis et al. | D12/146 |
| D. 304,917 | 12/1989 | Hinrichsen | D12/146 |

FOREIGN PATENT DOCUMENTS

| 0060306 | 3/1986 | Japan | 152/209 R |
| 0134315 | 6/1988 | Japan | 152/209 R |
| 0045203 | 2/1990 | Japan | 152/209 R |

OTHER PUBLICATIONS

"Pneumatic Tyre Design" E. C. Woods; 1952; p. 23.

Primary Examiner—Michael W. Ball
Assistant Examiner—Nancy T. Krawczyk
Attorney, Agent, or Firm—Robert W. Becker & Associates

[57] ABSTRACT

A vehicle tire of a radial carcass construction with a low cross-sectional profile having a tread portion that is reinforced by a belt layer is provided. The tread portion comprises a plurality of circumferential tread element bands in a center portion of the tread portion and one shoulder tread element row on either side of the center portion. The tread element bands are separated from one another and from the tread element rows in an axial direction of the vehicle tire by respective circumferential grooves that have straight edges. The tread element bands have notches that are distributed in a circumferential direction of the vehicle tire and are oriented at a slant relative to a center plane of the vehicle tire. The notches start at the circumferential grooves and end within the tread element bands. The shoulder tread element rows comprise tread elements that are separated from one another by transverse grooves and are arranged transverse relative to the center plane of the tire. The tread element bands comprise a central tread element band and respective adjacent tread element bands on either side, whereby at least the central tread element band has a central narrow circumferential groove arranged in the central tire plane. The central narrow circumferential groove has straight edges and is ¼ to ⅓ as wide and essentially as deep as the other circumferential grooves. At least the adjacent tread element bands are provided with narrow grooves that are spaced relative to one another by a circumferential length of a double tread element repeating unit whereby the narrow grooves are essentially as deep and ¼ to ⅓ as wide as the circumferential grooves. The narrow grooves and the notches are arranged in an alternating fashion.

10 Claims, 3 Drawing Sheets

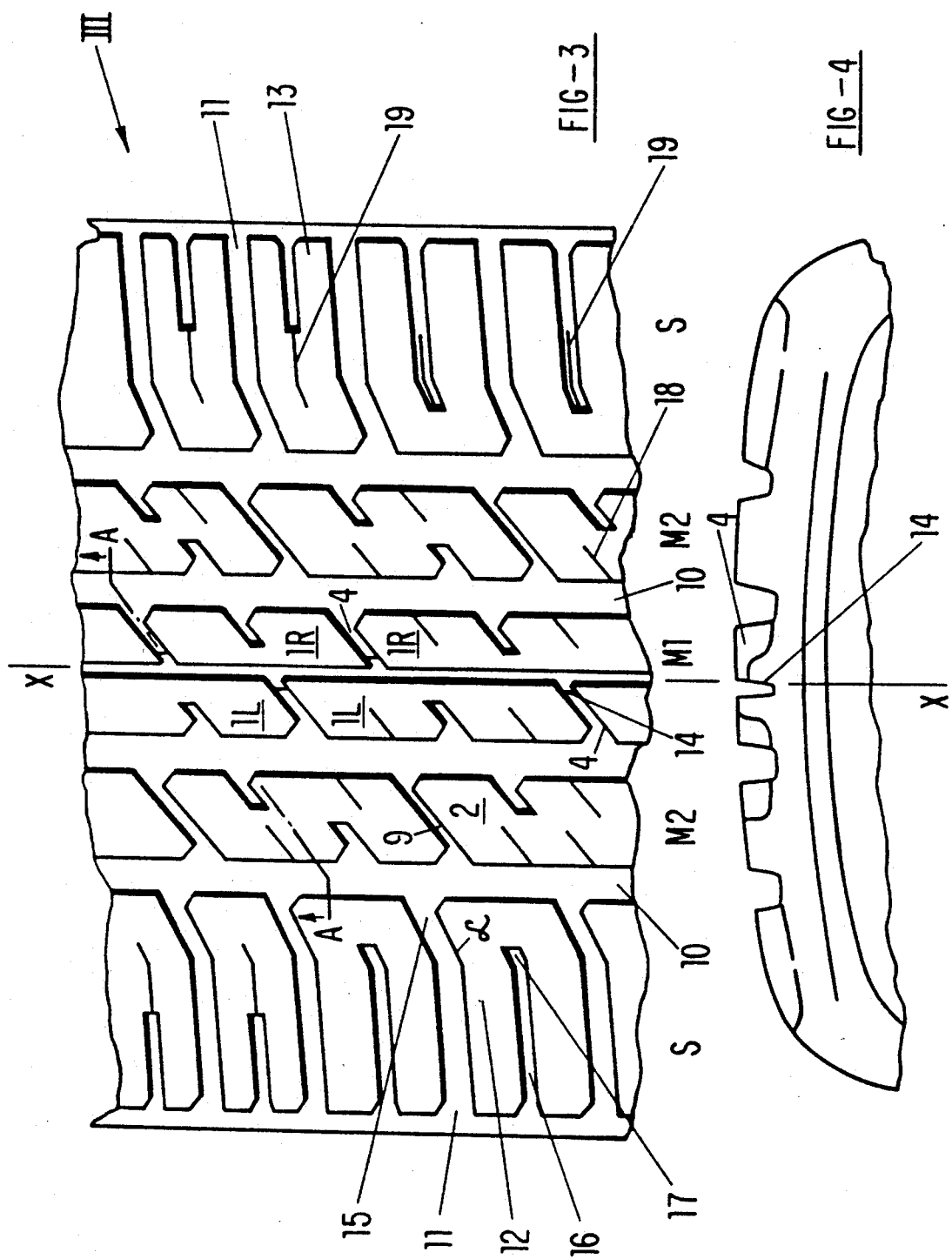

TIRE TREAD WITH SPACED CENTRAL TREAD NARROW GROOVES

BACKGROUND OF THE INVENTION

The present invention relates to a vehicle tire of a radial carcass construction with a low cross-sectional profile having a tread portion that is reinforced by a belt layer. The tread portion comprises a plurality of circumferential tread element bands in a center portion of the tread portion and one shoulder tread element row on either side of the center portion. The tread element bands are separated from one another and from the shoulder tread element rows in an axial direction of the vehicle tire by respective wide and deep circumferential grooves that have straight edges. The tread element bands have notches that are distributed in a circumferential direction of the vehicle tire and are oriented at a first angle relative to a center plane of the vehicle tire. The notches begin at the circumferential grooves and end within the tread element bands. The shoulder tread element rows comprise transverse tread elements that are separated from one another by transverse grooves and are arranged transverse relative to the center plane of the vehicle tire.

A tire tread of the aforementioned kind has been known from U.S. Pat. No. 4,387,754. The quality requirements for such vehicle tires of a radial carcass construction with a low cross-sectional profile include: excellent general driving characteristics, good performance on wet roads, and low noise emission of the tread portion. In order to realize these demands which are partially contradictory, a certain tread design is required as well as a modern tire construction. It has been demonstrated that wide tire treads, in general, exhibit excellent driving characteristics.

It is therefore an object of the present invention to improve the performance of vehicle tires especially on wet roads and reduce the noise emission by providing a suitable tire tread.

BRIEF DESCRIPTION OF THE DRAWINGS

This object, and other objects and advantages of the present invention, will appear more clearly from the following specification in conjunction with the accompanying drawings, in which:

FIG. 3 shows a section of a plan view of a modified tire tread; and

FIG. 4 shows a view along the line A—A of FIG. 3.

SUMMARY OF THE INVENTION

Figure 1:
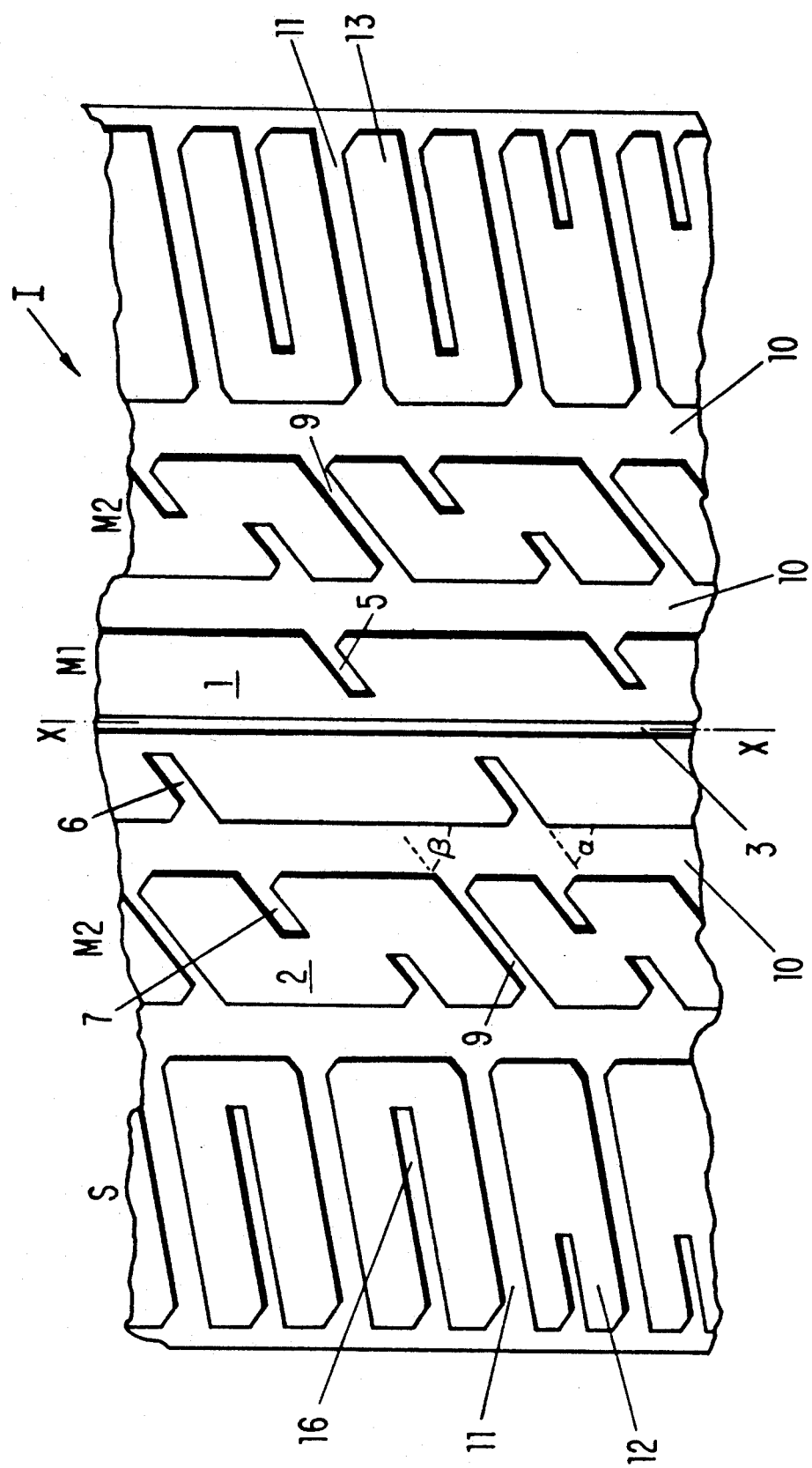
FIG. 1 shows a section of a plan view of a tire tread for a tire with a low cross-sectional profile.

The vehicle tire of the present invention is primarily characterized by a central tread element band and a respective adjacent tread element band on either side, with at least the central tread element band having a central narrow circumferential groove arranged in the central plane of the vehicle tire. The central narrow circumferential groove has straight edges and is ¼ to ⅓ as wide and essentially as deep as the circumferential grooves; at least the adjacent tread element bands are provided with first narrow grooves that are spaced relative to one another by twice a circumferential length of a tread element repeating unit, defined by the corresponding shoulder tread elements; i.e. double pitch, whereby the first narrow grooves are ¼ to ⅓ as wide and essentially as deep as the circumferential grooves; the first narrow grooves and the notches within the adjacent tread element bands are arranged in an alternating fashion.

Such a system comprising narrow grooves provides a positive/negative tread within the center portion of the tire tread which improves the characteristics of the vehicle tire such as the noise emission and the performance on wet roads. Such a tire tread, in conjunction with the aforementioned shoulder tread, is well suited to be employed at high speed and provides a sufficient safety margin under regular driving conditions as well as excellent performance on wet roads and a low noise emission.

The first narrow grooves are preferably disposed at a second angle relative to the central plane of the vehicle tire which corresponds essentially to the first angle of the notches of the adjacent tread element bands and is in the range of 30° to 45°.

In order to improve the performance on wet roads, the central narrow circumferential groove communicates with second narrow grooves that are disposed alternatingly to the right and to the left of the central narrow circumferential groove and are spaced relative to one another by twice the circumferential length of the tread element repeating unit (double pitch) and are slanted at a third angle in the range of 30° to 45°. The second narrow grooves are as wide and as deep as the central narrow circumferential groove. To stabilize such a tire tread with respect to forces acting in a circumferential and a transverse direction, the second narrow groove is provided with a connecting means in the area of an opening of the narrow groove into the central circumferential groove. The connecting means or connecting bridge connects neighboring tread elements of the central tread element band, whereby the connecting means has a lesser depth than the narrow groove and has a transition into the central circumferential groove.

The arrangement of the notches that end within the tread element bands and the second narrow grooves that branch off the central narrow circumferential groove is such that the second narrow grooves of neighboring tread element bands are spaced from one another at a small distance and the notches of neighboring tread elements bands are spaced from one another at a partially smaller and a partially greater distance in the circumferential direction. This ensures that at high speeds, especially under wet road conditions, a relatively low noise emission is present so that the properties with respect to the performance on wet roads and the noise emission are improved.

The transverse grooves of the shoulder portion of the tire tread are disposed at a fourth angle relative to the center plane of the vehicle tire which is smaller than 90°, preferably in the range of 60° to 85°. The opening of the transverse grooves into a respective adjacent one of the circumferential grooves is disposed between openings of the notches and the first narrow grooves into the circumferential grooves.

In order to improve the drainage and the general noise level within the shoulder portion of the tire tread the transverse grooves in the shoulder tread element rows have a bent portion, i.e., an opening toward the center plane of the tire tread that is disposed at a fifth angle relative to the central plane. This angle differs from the first and second angles and is preferably greater.

Due to these measures, the slanted edges of the slanted narrow groove system and the notches are aligned with the transverse grooves (via the bent portions) of the shoulder portion. Thus, the general performance as well as the drainage, the properties on wet roads, the noise emission and the abrasion resistance relative to forces acting in the circumferential and the transverse direction are improved.

Additionally, the transverse tread elements may be provided with a narrow notch. When the transverse grooves between the transverse tread elements are provided with bent portions, the narrow notches within the transverse tread elements are expediently provided with a bent portion also.

Within the tread element bands the tread elements are essentially S-shaped due to the notches provided therein. These S-shaped tread elements may be further provided with fine cuts or sipes, so-call lamellas. Such fine cuts or sipes may also be provided at the transverse tread elements of the shoulder tread element rows. Preferably, the fine cuts are oriented in the same direction as the edges of the tread elements, i.e., they are essentially slanted.

In a further embodiment, the respective ends of the transverse grooves that are facing away from the center plane, open axially outwardly in a funnel-shaped manner.

DESCRIPTION OF PREFERRED EMBODIMENTS

The present invention will now be described in detail with the aid of several specific embodiments utilizing FIGS. 1 to 4.

The tire tread of FIG. 1 comprises three tread element bands M1, M2 in the center portion: a central tread element band M1 in the form of a rib 1 and two tread element bands M2 to the right and the left, comprising tread elements 2. The tread element bands M1, M2 are separated from one another by wide and deep circumferential grooves 10.

The two shoulder portions of the tire tread are provided with respective shoulder tread element rows S, each comprising transverse tread elements 12, 13 respectively that are slanted at a (fourth) angle, smaller than 90°, preferably between 60° and 85°, relative to the center plane x—x of the vehicle tire and are separated from one another by transverse grooves 11. These shoulder tread element rows S are separated from the neighboring tread element bands M2 by further circumferential grooves 10.

In the center plane x—x of the vehicle tire, the central tread element band M1 is provided with a central narrow circumferential groove 3 that has straight edges. The central narrow circumferential groove 3 is ¼ to ⅓ as wide as the circumferential grooves 10, which corresponds, depending on the tire size, to approximately 1 to 4 mm. The central tread element band M1 is further provided with notches 5, 6 that are disposed alternatingly to the right and the left and are spaced apart at a distance corresponding to twice the circumferential length of the tread element repeating unit or double pitch, to the right and the left. The notches 5, 6 begin at the circumferential groove 10 and end within the tread element band M1.

The central narrow circumferential groove 3 as well as the notches 5, 6 have essentially the same depth. The notches 5, 6 are arranged relative to the center plane x—x of the vehicle tire at a first angle $\alpha$ that is in the range of 45° to 30°.

The tread element bands M2 have narrow grooves 9 that are arranged at a second angle $\beta$ relative to the center plane x—x of the vehicle tire. The narrow grooves 9 are spaced from one another at a distance corresponding to twice the circumferential length of the tread element repeating unit (double pitch). They divide the tread element band M2 into S-shaped tread elements 2. The narrow groove 9 is essentially as wide and essentially as deep as the circumferential groove 10. The tread elements 2 are provided with notches 7, 8 that correspond essentially to the notches 5, 6. Thus, a S-block configuration results.

The second angle $\beta$ corresponds essentially to the first angle $\alpha$, but may vary slightly from it by a few degrees. The transverse tread elements 12, 13 have groove-shaped narrow notches 16 of different lengths. These narrow notches 16 open into the outwardly facing area of the tire tread.

Figure 2:
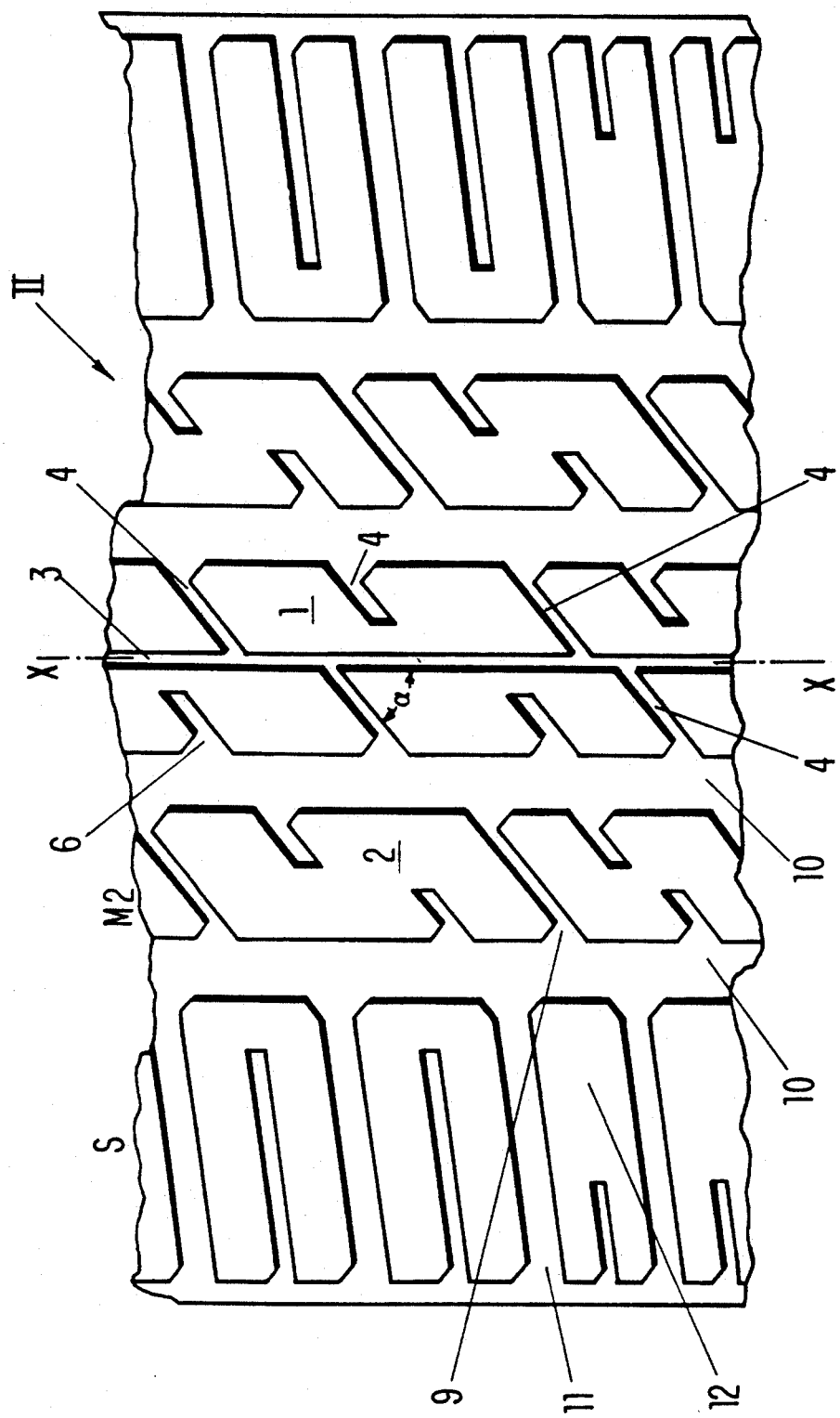
FIG. 2 shows a further embodiment.

The tire tread according to FIG. 2 corresponds essentially to the tire tread represented in FIG. 1. However, it has a further groove system in the central portion. This groove system is formed by the central narrow circumferential groove 3 and communicating narrow grooves 4 that are disposed to the right and the left at a distance corresponding to twice the circumferential length of the tread element repeating unit (double pitch). These narrow grooves 4 are arranged at a third angle $\gamma$ relative to the center plane x—x of the vehicle tire. The angle $\gamma$ corresponds essentially to the first and second angles $\alpha$ and $\beta$, however, it may vary by a few degrees. The narrow grooves 4 are essentially of the same depth as the circumferential grooves 10. Their width corresponds essentially to the width of the central narrow circumferential groove 3 and is, depending on the tire size, between 2 and 4 mm. The narrow grooves 4 and the notches 5, 6 are arranged in an alternating fashion. Due to the inventive tire tread design which comprises circumferential grooves, narrow grooves, notches and transverse grooves, a high speed tire with an excellent driving performance, especially on wet roads, and a low noise emission is provided.

The tire tread according to FIG. 3 represents a further embodiment of the inventive tire tread. The embodiment encompasses an improved drainage, which is achieved by providing transverse grooves 11 in the shoulder portion of the tire tread with a bent portion 15. Thus, the opening of the transverse groove 11 into the circumferential groove 10 is disposed at a fifth angle $\delta$ relative to the center plane x—x of the vehicle tire. The angle $\delta$ is greater than the angles $\alpha$, $\beta$, $\gamma$, and is in the range of 85° to 60°. Furthermore, the tread elements 1L, 1R of the central tread element band M1 formed by the central circumferential groove 3 are connected by a connecting means 14, when viewed from the central narrow circumferential groove 3. In the area of their opening into the central narrow circumferential groove 3 the narrow grooves 4 are provide with rubber material in the form of a connecting bridge or connecting means 14 that connect in the circumferential direction the neighboring tread elements 1L, respectively, 1R on either side of the equatorial plane of the tire. The depth of the second narrow groove 4 is reduced in this area but increases in the direction of the central narrow circumferential groove 3. This connecting means 14 ensures an area of increased stiffness in the direct vicinity of the central narrow circumferential groove 3, thereby increasing the stability with respect to forces that act on this portion of the tire tread. This stiffening portion or connecting means is represented in detail in FIG. 4 showing a view along the line A—A in FIG. 3.

All of the tread elements may be equipped with fine cuts or sipes 18 and 19, so-called lamellas. When the transverse grooves 11 are provided with a bent portion, the narrow notches 16 may also be provided with a bent portion 17.

Preferably, the edges of the of the transverse grooves 11 and narrow grooves 16 have slanted corners.

Due to such a tire tread a whole range of good performance characteristics of the respective vehicle tire is achievable which ensures a good general driving performance including a comfortable ride at high speeds. Special importance is placed on high drainage and high performance on wet roads as well as a low noise emission.

The present invention is, of course, in no way restricted to the specific disclosure of the specification, examples and drawings, but also encompasses any modifications within the scope of the appended claims.

What we claim is:

1. In a vehicle tire of a radial carcass construction with a low cross-sectional profile having a tread portion that is reinforced by a belt layer, whereby said tread portion comprises a plurality of circumferential tread element bands in a center portion of said tread portion and one shoulder tread element row with shoulder tread elements on either side of said center portion, with said tread element bands being separated from one another and from said shoulder tread element rows in an axial direction of said vehicle tire by respective wide and deep first circumferential grooves that have straight edges, and with said tread element bands having notches that are distributed in a circumferential direction of said vehicle tire and are oriented at a first angle relative to a center plane of said vehicle tire starting from said first circumferential grooves and ending within said tread element bands, and with said shoulder tread element rows comprising transverse tread elements that are separated from one another by transverse grooves and are arranged transverse relative to said center plane, the improvement wherein:

said tread element bands comprise a central tread element band and a respective adjacent tread element band on either side thereof, with at least said central thread element band having a central narrow second circumferential groove arranged in said central plane, said second circumferential groove having straight edges and being essentially as deep and ¼ to ⅓ as wide as said first circumferential grooves;

at least said adjacent tread element bands are provided with first narrow grooves that are spaced from one another by twice a circumferential length of a tread element repeating unit defined by said shoulder tread elements, with said first narrow grooves communicating with said first circumferential grooves and being essentially as deep and ¼ to ⅓ as wide as said first circumferential grooves, whereby said first narrow grooves and said notches within said adjacent tread element bands are arranged in an alternating fashion along each said first circumferential groove.

2. A vehicle tire according to claim 1, wherein said first narrow grooves are disposed at a second angle relative to said central plane, the value of said second angle corresponding essentially to the value of said first angle of said notches of said adjacent tread element bands and is in the range of 30° to 45°.

3. A vehicle tire according to claim 1, wherein said second circumferential groove communicates with second narrow grooves that are disposed alternatingly to the right and to the left of said second circumferential groove, with said second narrow grooves on the same side of said second circumferential groove and spaced relative to one another by twice said circumferential length of said tread element repeating unit and slanted at a third angle in the range of 30° to 45° relative to said second circumferential groove, said second narrow grooves being as wide and as deep as said second circumferential groove.

4. A vehicle tire according to claim 3, wherein said second narrow grooves, in the area of an opening thereof into said second circumferential groove, are provided with a connecting means for connecting in said circumferential direction neighboring tread elements of said central tread element band.

5. A vehicle tire according to claim 1, wherein said notches, with a respective opening thereof, are disposed alternatingly and spaced relative to one another by said circumferential length of twice said tread element repeating unit at said first circumferential grooves.

6. A vehicle tire according to claim 4, wherein said transverse grooves are disposed at a fourth angle relative to said center plane, said fourth angle being in the range of 60° to 85°, with a respective opening of said transverse grooves into a respective one of said first circumferential grooves being disposed between openings of said notches of said adjacent tread element bands and said first narrow grooves into said first circumferential grooves.

7. A vehicle tire according to claim 6, wherein said opening of said transverse grooves is disposed at a fifth angle relative to said central plane, said fifth angle being greater than said first and second angles.

8. A vehicle tire according to claim 1, wherein said transverse tread elements are provided with respective narrow grooves that have a bent portion.

9. A vehicle tire according to claim 1, wherein a respective end of said transverse grooves, that is facing away from said center plane, opens axially outwardly in a funnel-shaped manner.

10. A vehicle tire according to claim 1, wherein tread elements of said tread element bands and said transverse tread elements have fine cuts.

* * * * *